United States Patent
Geisbauer

(10) Patent No.: US 11,261,137 B2
(45) Date of Patent: *Mar. 1, 2022

(54) MANGANESE-DOPED NICKEL METHANIZATION CATALYSTS HAVING ELEVATED SULPHUR RESISTANCE

(71) Applicant: Clariant International Ltd, Muttenz (CH)

(72) Inventor: Andreas Geisbauer, Icking (DE)

(73) Assignee: CLARIANT INTERNATIONAL LTD, Muttenz (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/976,496

(22) PCT Filed: Mar. 6, 2019

(86) PCT No.: PCT/EP2019/055619
§ 371 (c)(1),
(2) Date: Aug. 28, 2020

(87) PCT Pub. No.: WO2019/170779
PCT Pub. Date: Sep. 12, 2019

(65) Prior Publication Data
US 2021/0047246 A1  Feb. 18, 2021

(30) Foreign Application Priority Data
Mar. 9, 2018 (DE) .................. 10 2018 105 539.0

(51) Int. Cl.
| | |
|---|---|
| *C07C 1/12* | (2006.01) |
| *B01J 21/04* | (2006.01) |
| *B01J 23/889* | (2006.01) |
| *B01J 37/02* | (2006.01) |
| *B01J 37/03* | (2006.01) |
| *B01J 37/08* | (2006.01) |

(52) U.S. Cl.
CPC ................ *C07C 1/12* (2013.01); *B01J 21/04* (2013.01); *B01J 23/8892* (2013.01); *B01J 37/0205* (2013.01); *B01J 37/035* (2013.01); *B01J 37/088* (2013.01); *C07C 2521/04* (2013.01); *C07C 2523/755* (2013.01); *C07C 2523/889* (2013.01)

(58) Field of Classification Search
CPC ............... C07C 1/12; C07C 2523/889; C07C 2523/755; C07C 2521/04
See application file for complete search history.

(56) References Cited

U.S. PATENT DOCUMENTS

| | | | |
|---|---|---|---|
| 6,103,206 A | 8/2000 | Taylor, Jr. | |
| 9,802,872 B2 | 10/2017 | Chen | |
| 2019/0381486 A1* | 12/2019 | Koehler | ................ B01J 37/031 |

FOREIGN PATENT DOCUMENTS

| | | |
|---|---|---|
| CN | 101745401 | 6/2010 |
| CN | 103480375 | 1/2014 |
| JP | S635034 | 1/1988 |

OTHER PUBLICATIONS

Bakar, Wan Azalee Wan abu et al. "Nickel oxide based supported catalysts for the in-situ reactions of methanation and desulfurization in the removal of sour gases from simulated natural gas"; Catalysis letters, 129, 2009, 1-2, 127-136, ISSN 1572-879X.

Zhao Kechao; Li Zhenhua; Bian Li; "CO2 methanation and co-methanation of CO and CO2 over Mn-promoted Ni/Al2O3 catalysts", Frontier of chemical science and engineering, 10, 2016, 2, 273-280, ISSN2095-0179; XP03596675.

Anmin Zhao et al: "Ni/Al2O3 catalysts for syngas methanation: Effect of Mn promoter", Journal of Natural Gas Chemistry, Bd. 21, Nr. 2, Mar. 1, 2012, pp. 170-177, XP055480082.

J. K. Dunleavy "Sulfur as a Catalyst Poison", Platinum metals review, Bd 50, No. 2, Apr. 1, 2006, p. 110.

Xianxian Wu et al: Removing hydrogen sulfide from hydrogen-rich gas streams by selective catalytic oxidation, preprints of papers—American chemical society, Division of Fuel Chemistry, Jan. 1, 2004l, pp. 893-894.

United States Environmental Protection Agency "Sulfur Dioxide Trends", Jun. 26, 2018.

* cited by examiner

*Primary Examiner* — Jafar F Parsa

(57) ABSTRACT

A process for the methanation of carbon monoxide and/or carbon dioxide in a feed stream containing carbon monoxide and/or carbon dioxide is disclosed. This is achieved by a process for the methanation of carbon monoxide and/or carbon dioxide in a feed stream containing carbon monoxide and/or carbon dioxide, hydrogen and more than 1 ppb of sulfur, using a catalyst comprising aluminum oxide, an Ni active composition and Mn. It has surprisingly The Mn-containing Ni catalyst has a high sulfur resistance and also a high sulfur capacity.

20 Claims, 3 Drawing Sheets

Figure 1:
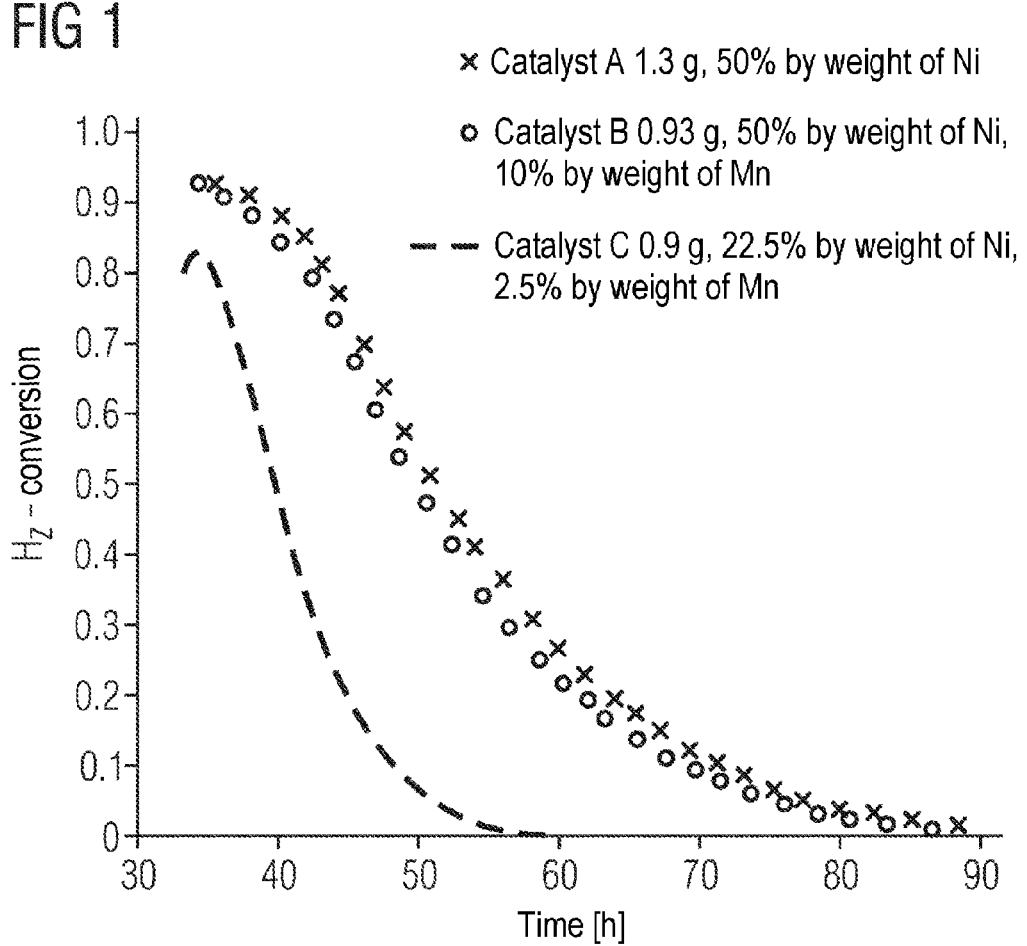

MANGANESE-DOPED NICKEL METHANIZATION CATALYSTS HAVING ELEVATED SULPHUR RESISTANCE

The subject matter disclosed in U.S. patent application Ser. No. 16/479,283 and the claimed invention were made by or on behalf of parties to a joint research agreement between Clariant Produkte (Deutschland) GMbH, Wacker Chemie AG and Technische Universitat Munchen.

The supply of energy by means of the renewable energies photovoltaics and wind energy suffers from the problems of weather-dependent and time-of-day-dependent fluctuations in electric power production. To ensure security of supply, a way to equalize weather-dependent and time-of-day-dependent fluctuations in electric power production has to be found. One possible method of storing the energy chemically is the power-to-gas process in which surplus power is used to split water into hydrogen and oxygen by electrolysis. Hydrogen, in which the energy is stored after the electrolysis of water, can itself be stored or transported to the consumer only at great expense. After the power-to-gas process, the hydrogen is therefore reacted in a further step with carbon dioxide, which acts as climate-damaging greenhouse gas in the atmosphere, in the methanation reaction to form methane and water. Methane can easily be stored in existing infrastructures which have capacities for storage in the range of several months, be transported virtually without losses over relatively great distances and be converted back into electric power at times when energy is required. The methanation reaction, which is associated with liberation of a large amount of energy and usually proceeds in the presence of a catalyst, forms the key part of the process. The highly exothermic nature of the reaction (enthalpy of reaction=−165 kJ/mol) results in two direct problems. Firstly, the thermodynamic equilibrium limits the maximum achievable yield of methane at high temperatures. For introduction of methane into the natural gas grid in Germany, a purity of 95% is required. This leads to a need for a high catalyst activity, so that relatively high yields of methane can be achieved at low temperatures at reaction pressures employed in industry.

To ensure a constant product gas quality in the hydrogenation of $CO_2$ and CO to give methane over nickel-based catalysts, a very high, constant activity and selectivity of the catalyst is required. However, activity and selectivity of a catalyst decrease over time in industrial use due to various deactivation mechanisms.

Apart from thermal and mechanical deactivation processes, chemical processes caused by sulfur in the gas stream play a particularly important role.

As is known from industrial practice and the literature, even very small proportions of hydrogen sulfide in the order of <100 ppb lead to poisoning of nickel catalysts, associated with decreases in activity. Here, $H_2S$ reacts with nickel, so that a poisoning front of nickel sulfide migrates through the catalyst bed. The formation of nickel sulfide can be described by at least two $Ni_xS_y$ phases: $Ni_3S_2$ (heazlewoodite) and $Ni_3S_4$ (polydymite).

Depending on the origin of the $CO_2$ or CO used, this contains corresponding amounts of impurities. In the case of the purification of $CO_2$ from biogas plants, which contains $H_2S$ in amounts in the order of from 200 to 1000 ppm, this is at present adsorptively prepurified in a costly manner, first and foremost to reduce sulfur contamination such as $H_2S$ to a minimum.

In large industrial SNG plants (SNG="synthetic natural gas") based on gasification of coal, too, the methanation reaction is of central importance. The hydrogen obtained by means of the gasification of coal and the subsequent shift reaction ($CO+H_2O \rightarrow CO_2+H_2$) is purified, for example by wet scrubbing with cold methanol, and contains low levels of sulfur contamination in the order of <100 ppb. However, even these low levels of sulfur contamination can have an adverse effect on the period of operation of the subsequent synthesis reactors.

Catalysts having increased sulfur resistance could reduce the prepurification outlay or increase the period of operation of the synthesis reactor, with a positive effect on the economics of the overall plant.

U.S. Pat. No. 4,132,672 A discloses an improved process for the conversion of hydrogen and carbon monoxide into a methane-enriched gas, in which process a supported nickel catalyst promoted by the addition of a small percentage of iridium metal, typically from 0.1 to 1.0% by weight, is used. This promoted catalyst is very active in methanation and has good resistance to poisoning by sulfur compounds.

Since the methanation of CO and $CO_2$ proceeds highly exothermically, catalysts having an increased resistance to sulfur at low temperatures are desirable in view of the reaction equilibrium, but this is very challenging because of the exothermic nature of the formation of NiS. At higher temperatures (>600° C.), the binding of sulfur to nickel catalysts is reversible, but the position of the reaction equilibrium in the direction of high proportions of methane in the product gas is unfavorable.

It is an object of the invention to provide a process for the effective methanation of carbon monoxide and/or carbon dioxide, with high selectivity and activity and also improved stability in sulfur-containing feed streams.

This object is achieved by a process for the methanation of carbon monoxide and/or carbon dioxide in a feed stream containing carbon monoxide and/or carbon dioxide, hydrogen and more than 1 ppb of sulfur, using a catalyst comprising aluminum oxide, an Ni active composition and Mn, characterized in that the molar ratio of Ni/Mn in the catalyst is in the range from 1.0 to 15.0, preferably from 2.0 to 12.0, particularly preferably from 3.0 to 10.0 or especially preferably in the range from 3.5 to 5.5 or from 7.5 to 9.5.

It has surprisingly been found that an Mn-containing Ni catalyst has a high sulfur resistance and also a high sulfur capacity. The catalyst which is employed in the process of the invention displays not only an improved capability for catalyzing the methanation reaction despite the presence of sulfur ("sulfur resistance"), but at the same time the capability of absorbing and irreversibly binding sulfur ("sulfur capacity").

In addition, the invention provides a process for the methanation of carbon monoxide and/or carbon dioxide in a feed stream containing carbon monoxide and/or carbon dioxide, hydrogen and more than 1 ppb of sulfur, where the feed stream is passed through a reactor containing a catalyst which comprises an Ni active composition and Mn and has a molar ratio of Ni/Mn in the catalyst in the range from 1.0 to 15.0, preferably from 2.0 to 12.0, particularly preferably from 3.0 to 10.0 or especially preferably in the range from 3.5 to 5.5 or from 7.5 to 9.5, characterized in that the catalyst absorbs the sulfur present in the feed stream and at the same time catalyzes the methanation reaction.

Furthermore, the invention provides for the use of a catalyst comprising aluminum oxide, an Ni active composition and Mn, characterized in that the molar ratio of Ni/Mn in the catalyst is in the range from 1.0 to 15.0, preferably from 2.0 to 12.0, particularly preferably from 3.0 to 10.0 or especially preferably in the range from 3.5 to 5.5 or from 7.5 to 9.5, for the methanation of carbon monoxide and/or carbon dioxide by means of gaseous hydrogen in the presence of more than 1 ppb of sulfur.

The catalyst preferably absorbs more than 70%, more preferably more than 80%, of the sulfur present in the feed stream during the process of the invention, i.e. the product stream contains 70 or 80% less sulfur than the feed stream during the process. Particular preference is given to the catalyst completely absorbing the sulfur in the feed stream during the process of the invention: the product stream then no longer contains any sulfur.

The catalyst of the invention is particularly suitable for the methanation of carbon monoxide and/or carbon dioxide by means of hydrogen in the presence of more than 1 ppb, preferably more than 4 ppb, particularly preferably more than 10 ppb, of sulfur. One ppb of sulfur here corresponds to one part by volume in a billion ($10^{-9}$) of the sulfur-containing molecule, with it being assumed as an approximation that each sulfur-containing molecule has only one sulfur atom. In particular, the proportion of sulfur in the process of the invention is in the range from 1 ppb to 300 ppm, preferably from 4 ppb to 10 ppm, of sulfur. One ppm of sulfur here corresponds to one part by volume in a million ($10^{-6}$) of the sulfur-containing molecule, with it being assumed as an approximation that each sulfur-containing molecule has only one sulfur atom.

The methanation of carbon dioxide can be represented by the following reaction equation:

$$4H_2+CO_2 \rightarrow CH_4+2H_2O$$

The methanation of carbon monoxide can be represented by the following reaction equation:

$$3H_2+CO \rightarrow CH_4+H_2O$$

The methanation is generally carried out at temperatures of from 180° C. to 600° C. In the process for carrying out the methanation, the feed gas, which contains carbon dioxide or carbon monoxide or a mixture of the two, is brought into contact with the catalyst at a temperature from above 180° C. to 600° C.

The catalyst contains aluminum oxide, an Ni active composition and Mn, and the Ni/Mn ratio can be, especially in the case of a catalyst prepared by coprecipitation, in the range from 2.0 to 6.0, particularly preferably from 3.5 to 5.5 or especially preferably in the range from 4.0 to 5.0. As an alternative, the Ni/Mn ratio is, especially in the case of the catalyst prepared by impregnation, in the range from 6.0 to 10.0, preferably from 7.5 to 9.5 and particularly preferably from 8.0 to 9.0.

The aluminum oxide does not have to be stoichiometric $Al_2O_3$, but can instead be a nonstoichiometric aluminum oxide, with preference being given to it being gamma-$Al_2O_3$.

The promoter Mn can be present entirely or partially in the Ni active composition. The catalyst can contain further promoters in addition to Mn, but can also contain exclusively the promoter Mn. The oxidation states of Al, Ni and the promoters can vary depending on the treatment of the catalyst. Al, Ni and the promoters are typically present as metal cations (e.g. $Al^{3+}$, $Ni^{2+}$, $Mn^{2+}$, $Mn^{4+}$). After calcination, e.g. in air, high oxidation states or the maximum oxidation states can be attained. If the catalyst is reduced at temperatures above room temperature, e.g. under reaction conditions by means of hydrogen, Al, Ni and the promoters can acquire lower oxidation states or occur partially or entirely in the oxidation state 0. The charge of the metal cations is balanced by oxygen anions ($O^{2-}$).

The catalyst according to the invention can contain further components in addition to aluminum oxide ($AlO_x$ where $x \leq 1.5$), Ni and Mn (plus the oxygen anions necessary to balance the charge), but can also consist exclusively of aluminum oxide, Ni and Mn. The Ni active composition can also contain further promoters in addition to Mn, but can also contain exclusively the promoter Mn. The Ni active composition preferably does not contain any elements selected from among B, Ta, In, Cu, Ce, Cr, Bi, Fe, P, Sb, Sn, Si, Ti, Zr, Co, Rh, Ru, Ag, Ir, Pd and Pt. The Ni active composition preferably does not contain any noble metal.

In the case of the catalyst prepared by impregnation, the atomic (i.e. molar) ratio of Al/Ni is preferably greater than 2, particularly preferably greater than 2.7, with the molar ratio of Al/Ni being very particularly preferably in the range from 2 to 9, more preferably from 2.3 to 5.

In the case of the catalyst prepared by coprecipitation, the molar ratio of Al/Ni is preferably in the range from 0.1 to 0.9, more preferably from 0.3 to 0.7, with the molar ratio of Al/Ni particularly preferably being approximately 0.45.

The catalysts according to the invention can advantageously have crystallites having a diameter of less than 20 nm, preferably less than 10 nm, in the Ni active composition. The Ni active composition can also consist entirely or significantly of crystallites having a diameter below 20 nm, preferably below 10 nm. The Ni active composition is preferably present in a metallic state.

The $CO_2$ uptake capacity of the catalysts at 35° C. can be greater than 150 μmol/g and is preferably in the range from 150 to 350 μmol/g, particularly preferably from 180 to 260 μmol/g.

The BET surface area ($S_{BET}$) of the catalyst according to the invention can be greater than 100 m²/g, preferably greater than 200 m²/g, or in the range from 100 to 200 m²/g, preferably in the range from 150 to 180 m²/g.

The specific metal surface area ($S_{met}$) of the catalyst according to the invention is preferably greater than 10 m²/g, more preferably greater than 20 m²/g and preferably in the range from 20 m²/g to 70 m²/g. In the case of the catalyst produced by coprecipitation, the specific metal surface area ($S_{met}$) is preferably in the range from 30 to 70 m²/g, particularly preferably from 40 to 60 m²/g. In the case of the catalyst produced by impregnation, the specific metal surface area ($S_{met}$) is in the range from 20 to 80 m²/g, preferably from 25 to 70 m²/g or from 30 to 60 m²/g.

The catalyst used in the process of the invention is preferably present in a reactor and in this forms a catalyst bed. The feed gas flows through the reactor and thus comes into contact with the catalyst. At the same time, the reactor is heated so that the necessary reaction temperature of the catalyst is attained.

Owing to its increased sulfur capacity in addition to its catalytic function, the catalyst simultaneously acts as sulfur trap ("trap" function). The catalyst located near the reactor inlet in the catalyst bed will absorb the sulfur and thus protects the downstream catalyst from sulfur poisoning. At the same time, the catalyst loaded with sulfur at least partially retains its activity in the methanation reaction. The catalyst used in the process of the invention has the advantage of an increased sulfur uptake capacity, so that the function as sulfur trap is realized in addition to the function as methanation catalyst. The function as methanation catalyst is increased as a consequence of the improved function as sulfur trap. Ideally, the sulfur present in the feed gas will be completely absorbed in the front region of the catalyst bed, so that the feed gas no longer contains any sulfur in the downstream region of the catalyst bed and accordingly no deactivation by sulfur takes place there.

The catalyst used in the process of the invention can be produced by coprecipitation. In the production of the catalyst by coprecipitation, at least one solution containing Al, Ni and Mn in dissolved form is admixed with a precipitation reagent in order to obtain a precipitate.

The production of the catalysts by coprecipitation comprises, for example, the following steps:
a) coprecipitation from a solution containing Al, Ni and Mn in dissolved form in order to obtain a precipitate,
b) isolation of the precipitate from step a),
c) drying of the isolated precipitate from step b) and
d) calcination of the dried precipitate from step c).

Preference is here given to the solution in step a) being an aqueous solution and Al, Ni and Mn being present in dissolved form as ionic compounds in the aqueous solution.

As an alternative, the catalyst according to the invention can also be prepared by impregnation. In this case, the catalyst according to the invention is, for example, produced by simultaneous impregnation of a suitable aluminum oxide support with nickel and manganese.

The effect of improved sulfur resistance and sulfur capacity is observed both for precipitated (coprecipitated) catalysts and impregnated catalysts. Impregnated catalysts normally cannot be produced with Ni contents which are as high as those of precipitated catalysts, since the uptake of nickel in the case of impregnation is limited by the volume of the pores of the aluminum oxide.

It has surprisingly been found that the sulfur capacity of an impregnated catalyst is, based on the amount of Ni used, even somewhat greater than in the case of a coprecipitated catalyst. This can be seen in FIG. 2 in which the amount of sulfur taken up has been normalized to the weight of catalyst. Despite a lower metal loading of catalyst C, a similar increase in mass to that in the case of catalyst A is obtained.

FIG. 1: decrease in the activity of the catalysts A to C during the catalytic test reaction (Test 1).

Figure 2:
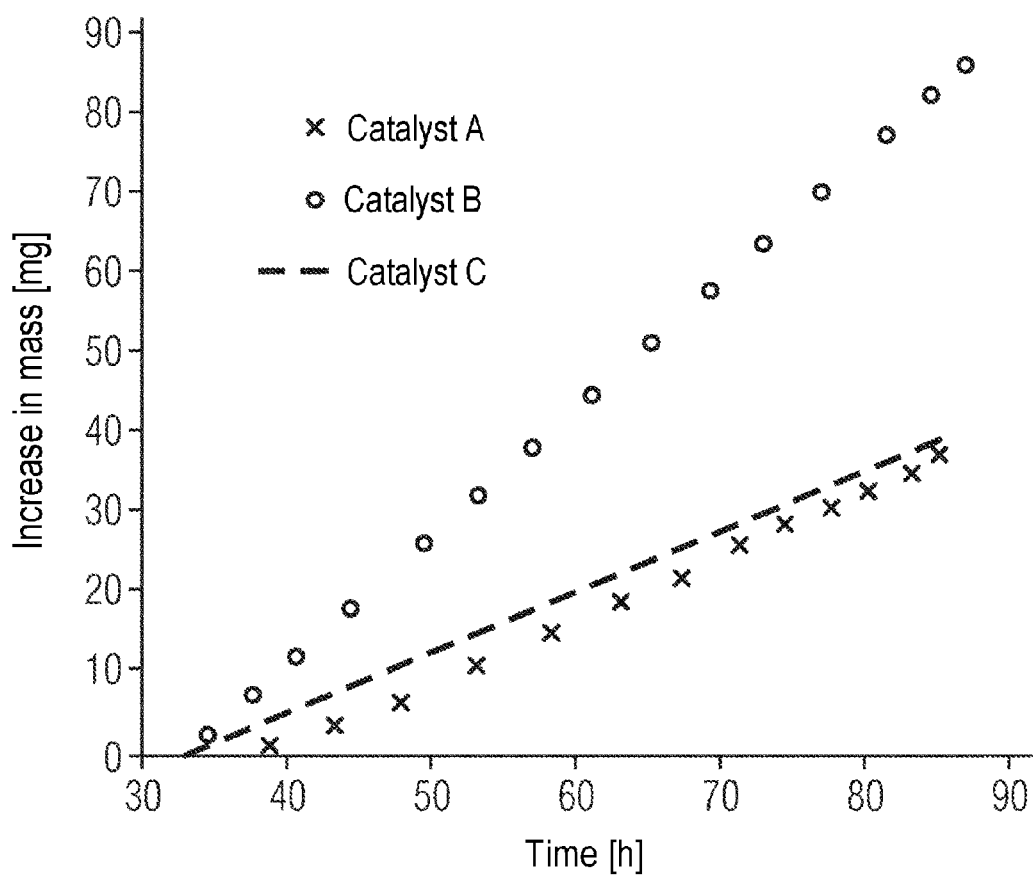

FIG. 2: increase in mass of the catalysts A to C due to uptake of sulfur during the catalytic test reaction, normalized to the weight of catalyst (Test 1).

Figure 3:
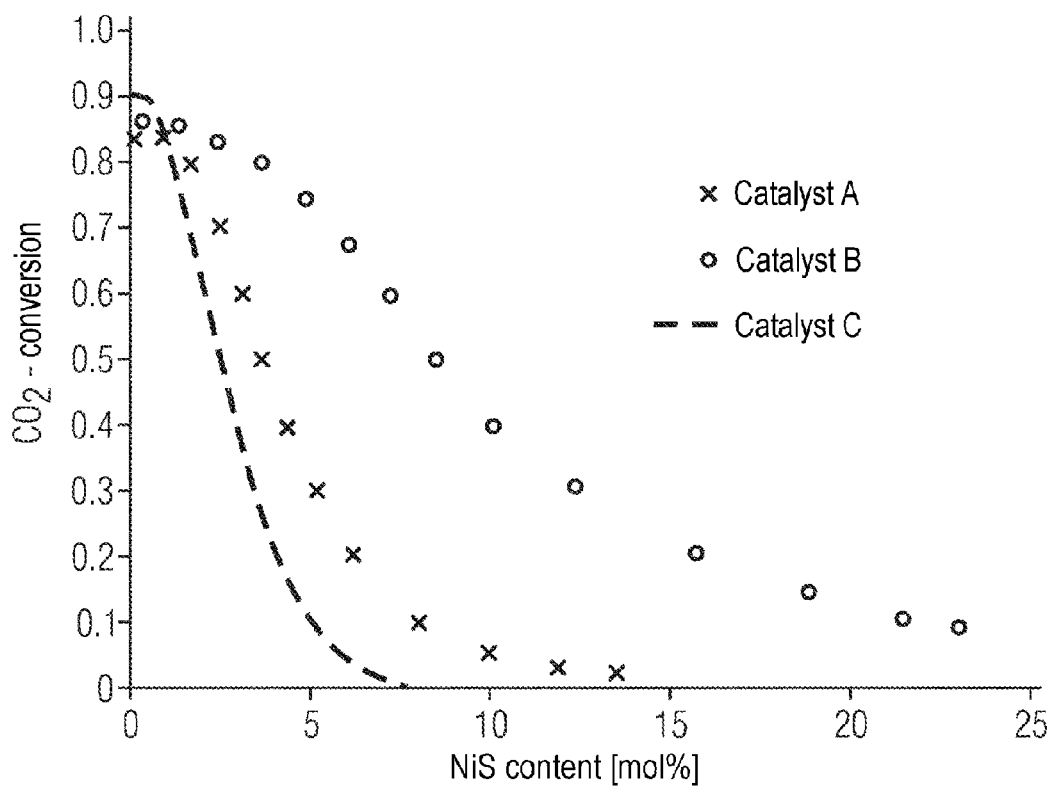

FIG. 3: decrease in the activity as a function of the uptake of sulfur during the catalytic test reaction (Test 1, with the assumption that nickel sulfide is formed).

Figure 4:
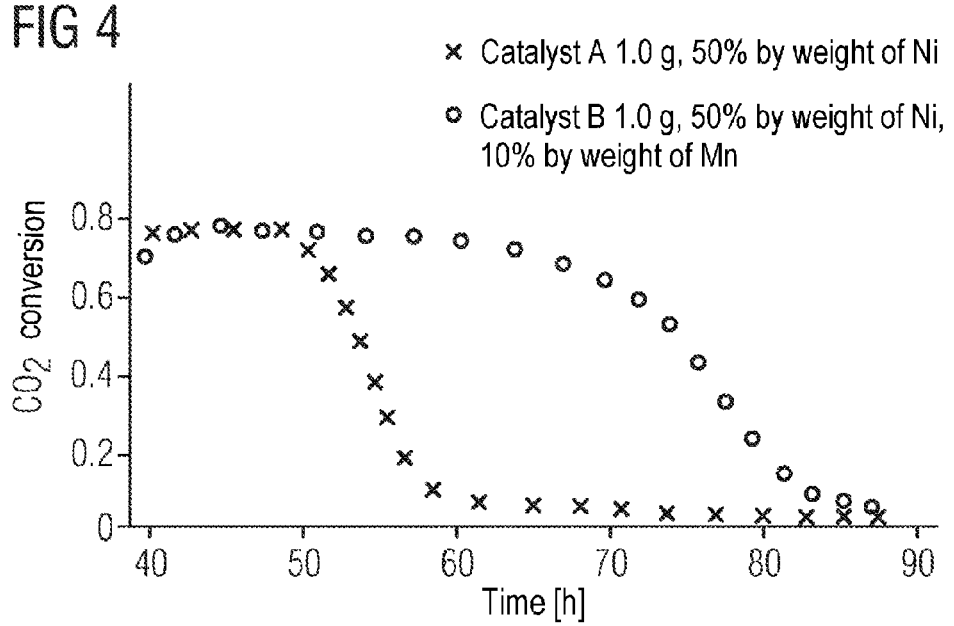

FIG. 4: decrease in the activity of the catalysts A and B during the catalytic test reaction (Test 2).

METHODS

Elemental Analysis

The determination of the composition of the calcined catalysts was carried out by optical emission spectroscopy by means of inductively coupled plasma (ICP-OES). 50 mg of catalyst were dissolved in 50 ml of 1 molar phosphoric acid (VWR, A.R.) at 60° C. In order to dissolve manganese dioxide formed, 50 mg of $Na_2SO_3$ (Sigma Aldrich, A.R.) were added to the solution. After cooling, the solutions were diluted by a factor of 1/10, admixed to the same concentration with $Na_2SO_3$ and filtered by means of 0.1 µm filters (Pall). The calibration solutions were made up with concentrations of 1, 10 and 50 mg l$^{-1}$ (Merck). Determination of the metal concentrations was carried out by means of an Agilent 700 ICP-OES.

Determination of the Specific Surface Area

The determination of the specific surface areas of the catalysts ($S_{BET}$) was carried out by means of $N_2$-BET analysis on a NOVA 4000e (Quantachrome). For this purpose, 100 mg of catalyst were degassed at 120° C. for 3 hours and adsorption and desorption isotherms were subsequently recorded in the $p/p_0$ range from 0.007 to 1. To determine the BET surface area, the data points in the $p/p_0$ range from 0.007 to 0.28 were employed.

Hg Pore Volume

The pore distribution and the pore volume of the catalyst particles were determined using a mercury porosimeter: Pascal 440 from Thermo Electron Corporation in accordance with DIN 66133. Here, the sample was evacuated beforehand for 30 minutes at room temperature. Samples in the range from 600 to 900 mg were measured and the pressure was increased to 2000 bar.

Chemisorption

Chemisorption experiments were carried out on an Autosorb 1C (Quantachrome). Before the measurement, 100 mg of catalyst were activated at 500° C. in 10% of $H_2$ in $N_2$ for 6 hours. The heating ramp was 2 Kmin$^{-1}$.

The determination of the metal surface area ($S_{MET}$) was effected in accordance with DIN 66136-2 (version 2007-01) and was carried out by means of $H_2$ chemisorption at 35° C. For this purpose, 20 adsorption points were recorded equidistantly from 40 mmHg to 800 mmHg. The equilibration time for the adsorption was 2 minutes, and that for thermal equilibrium was 10 minutes. To determine the metal surface area, a metal atom/H stoichiometry of 1 was assumed. For $CO_2$ chemisorption measurements, the equilibration time for the adsorption was set to 10 minutes with otherwise unchanged parameters. Before recording of the chemisorption data, a possible kinetic inhibition of the $CO_2$ chemisorption under these conditions was experimentally ruled out. Metal surface areas and $CO_2$ uptake capacities were extrapolated according to the extrapolation method to a pressure of 0 mmHg.

Synthesis

The catalysts A and B were produced by coprecipitation at a loading with nickel of 50% by weight, which in the case of catalyst A leads to a molar ratio of aluminum to nickel of 0.75 and in the case of the manganese-containing catalyst B leads to a molar ratio of Al/Ni of 0.47. To examine the effect of manganese on the catalyst behavior, manganese(II) nitrate was added to the salt solution of nickel nitrate and aluminum nitrate during the catalyst synthesis. The purity of all chemicals used was A.R. Water was purified by means of a Millipore filter system and the purity was verified by means of conductivity measurements. The synthesis was carried out in a double-walled, 3 l capacity stirred vessel. The double wall filled with water allowed, with the aid of a thermostatic bath, maintenance of the temperature of the synthesis mixture as 30° C., and two baffles ensured improved mixing. A precision glass stirrer at 150 revolutions per minute was used for stirring. For the synthesis, 1 l of $H_2O$ was placed in the stirred vessel and set to a pH=9±0.1. The mixture of the dissolved nitrates was metered in at 2.5 ml min$^{-1}$. At the same time, controlled addition of the precipitation reagent served to maintain the pH. As starting materials, use was made of one molar solutions of the respective nitrates ($Ni(NO_3)_2*6H_2O$, $Al(NO_3)_2*9H_2O$ and $Mn(NO_3)_2*4H_2O$). For catalyst B, these were mixed in a molar ratio of Ni to Mn of 4.6:1 and of Al to Ni of 0.45 to give a total volume of 120 ml min$^{-1}$, before dropwise introduction into the reactor was carried out. A mixture of equal volumes of the solutions 0.5M NaOH and 0.5M Na$_2$CO$_3$, which were metered using a titrator, served as precipitation reagent. The suspension was aged overnight in the mother liquor while stirring continually, the precipitate was subsequently filtered off and washed with H$_2$O until the filtrate had a neutral pH. After drying at 80° C. overnight in a drying oven, the dried precipitate (precursor) was heated at a heating rate of 5 K min$^{-1}$ to 450° C. and calcined under synthetic air for 6 hours.

The catalyst C was produced by triple impregnation with subsequent calcination in each case. 3022.0 g of Ni(NO$_3$)$_2$×6H$_2$O (98%), 307.9 g of Mn(NO$_3$)$_2$×4H$_2$O (98.5%) were placed in a 5 l glass beaker. The mixture was made up to a volume of about 2900 ml with deionized water and stirred by means of a propeller stirrer until a clear solution had been obtained. The solution was then made up to the required total volume of 3441 ml with deionized water.

First impregnation: 1879.3 g of gamma aluminum oxide ⅛" extrudate (corresponding to 3.6 l; bulk density: 522 g/l; loss on ignition: 4.22%) were placed in a closable vessel. 1349 ml of impregnation solution, which corresponds to the maximum amount of solution at which a supernatant solution is not yet formed, were added slowly and in small amounts. In between, the vessel was always closed again and shaken/homogenized. After the entire solution had been added, the mixture was shaken for a further two minutes.

First calcination: the impregnated extrudates were transferred to porcelain dishes and heated at 2° C./min to 120° C. and dried in air at this temperature for 6 hours. The impregnated extrudates were subsequently heated at 2° C./min to 240° C. and calcined at this temperature in air for 4 hours.

Second impregnation: the extrudates which had been impregnated once were placed in a closable vessel. 1147.0 ml of impregnation solution, which corresponds to the maximum amount of solution at which a supernatant solution is not yet formed, were added slowly and in small amounts. In between, the vessel was always closed again and shaken/homogenized. When the entire solution had been added, the mixture was shaken for a further two minutes.

Second calcination: the impregnated extrudates were transferred to porcelain dishes and heated at 2° C./min to 120° C. and dried at this temperature in air for 6 hours. The impregnated extrudates were then heated at 2° C./min to 240° C. and calcined at this temperature in air for 4 hours.

Third impregnation: the extrudates which had been impregnated twice were placed in a closable vessel. 944.3 ml of impregnation solution, which corresponds to the maximum amount of solution at which a supernatant solution is not yet formed, were added slowly and in small amounts. In between, the vessel was always closed again and shaken/homogenized. When the entire solution had been added, the mixture was shaken for a further two minutes.

Third calcination: the impregnated extrudates were transferred to porcelain dishes and heated at 2° C./min to 120° C. and dried at this temperature in air for 6 hours. The impregnated extrudates were then heated at 2° C./min to 240° C. and calcined at this temperature in air for 4 hours.

Thermogravimetric Analysis and Catalytic Test Reaction

Thermogravimetric analysis (TGA) was used to examine the deactivation by hydrogen sulfide. Here, the catalyst bed to be examined is introduced into a heated reactor (1.53 ml) through which forced flow occurs and supplied with feed gases (79.5% by volume of H$_2$, 20.5% by volume of CO$_2$; H$_2$S content of starting material 43 ppm at T=270° C., p=6 barg and SV ("space velocity" about 16 000 1/h). The flow behavior through the bed resembles that of tube reactors. Mass changes during the catalytic process can be detected by means of discontinuous, contactless weighing (precision=±10 μg) via a magnetic suspension coupling. At the same time, the catalytic activity was evaluated by determining the product gas composition. For this purpose, a substream of the product gas was analyzed using a mass spectrometer. The results are shown under "Catalytic test reactions", "Test 1" and "Test 2". The experimental conditions were kept constant during the series of experiments to ensure comparability of the various catalysts examined. Since the catalysts are obtained in oxidic form from the synthesis, they firstly have to be reduced in a stream of H$_2$ in order to produce the catalytically active, metallic phases before commencement of the tests. Reduction is carried out until the weight remains constant. The reported weights of the catalysts used relate to this weight after reduction, which is lower than the original weight due to the conversion of NiO into Ni and MnO$_2$ into Mn:

Test 1: catalyst A: 1.27 g, catalyst B: 0.93 g, catalyst C: 0.90 g. The normalized H$_2$ conversion (0 corresponds to 0% conversion, 1 corresponds to 100% conversion) is shown.

Test 2: catalyst A: 1.02 g, catalyst B: 1.05 g of catalyst

EXAMPLES

Example 1: Synthesis of the Catalysts

Three catalyst samples were prepared in accordance with the synthesis described in the method part, with catalyst A being a comparative sample without manganese, while the catalysts B and C contain manganese. The three catalysts have the properties summarized in Table 1.

TABLE 1

Analytical data for the catalysts examined

| Catalyst | Ni [% by weight] | Mn [% by weight] | Surface area of Ni [m$^2$/g] | Crystallite size [A°] | Ni dispersion [%] | Pore volume [mm$^3$/g] | S uptake [% by weight] | Catalyst shape | Weight used [g] |
|---|---|---|---|---|---|---|---|---|---|
| A (comparison) | 50 | — | 35 | 79 | 10 | 210 | 1.5 | 1.8 × 3.6 pellet | TEST 1: 1.27 TEST 2: 1.02 |
| B | 50 | 10 | 51 | 55 | 15 | 255 | 5.1 | 3 × 3 pellet | TEST 1: 0.93 TEST 2: 1.05 |
| C | 22 | 2.5 | 32 | 39 | 21 | 233 | 3.2 | ⅛" extrudate | TEST 1: 0.9 |

Example 2: Catalytic Test Reactions

Test 1

The results from Test 1 are shown in FIG. 1. The $H_2$ conversion decreases with increasing time on stream and catalyst poisoning for all catalysts examined. In the case of catalyst A and catalyst B, each having a loading of 50% by weight of Ni, the activity decrease is very similar, but the weight of Mn-promoted catalyst B at 0.93 g compared to 1.27 g for catalyst A was significantly smaller and the catalytic results are not normalized to the weight used. In the case of catalyst C, the activity decreases more quickly because of the nickel loading which is only about half as great.

Test 2

The results from Test 2 are shown in FIG. 4. The $CO_2$ conversion decreases with increasing time on stream and catalyst poisoning for both catalysts examined. In contrast to the results in FIG. 1, the same catalyst weight of 1.0 g and the same size of catalyst particles were employed for the two catalysts A and B for the purpose of better comparability. The weight of catalyst A and of catalyst B was 1.02 and 1.05 g, respectively. Catalyst B displays significantly improved deactivation behavior. According to the result from Test 2, the additional amount of 10% by weight of manganese in catalyst B thus leads to an approximate doubling of the time to deactivation of catalyst B compared to catalyst A.

Example 3: Sulfur Uptake During the Catalytic Test Reaction

During the catalytic test reactions in example 2, the uptake of sulfur by all three catalyst samples A, B and C was in each case measured at the same time. This can be seen from the measurement data in FIG. 2; the sulfur uptake was normalized to the catalyst weight. Surprisingly, the uptake of sulfur by catalyst B is significantly higher than in the case of catalyst A. Even in the case of catalyst C, the sulfur uptake is increased compared to the reference catalyst catalyst A without manganese, even though catalyst C has a significantly lower nickel loading. The additional content of manganese of the two catalysts B and C surprisingly leads to an increase in the sulfur uptake.

This observation is also confirmed by the analytical determination of the sulfur content of the catalysts after complete deactivation. The analytical results for the S uptake from the TGA test and the chemical analysis are summarized in table 2. While the weighing of the TGA analysis gives an integrated value for the amount of S taken up, the used catalyst after Test 2 was complete was taken out in layers. By means of subsequent chemical analysis, the S uptake can then be determined in a positionally resolved manner and a corresponding loading profile can be determined. It can be clearly seen here that the sulfur uptake has the highest value in the upper part of the reactor crucible of the TGA, and the loading with sulfur decreases gradually in the direction of the reactor outlet. The chemical analysis was carried out by inductive combustion of the sample in a stream of oxygen to form $SO_2$ and subsequent, quantitative infrared analysis of a characteristic $SO_2$ band.

TABLE 2

Determination of the sulfur uptake by means of TGA analysis and subsequent chemical analysis of the used catalysts after removal from the experimental reactor.

|  |  | Unit | Catalyst A | Catalyst B | Catalyst C |
|---|---|---|---|---|---|
| Weight of reduced catalyst | Test 1 | [g] | 1.27 | 0.93 | 0.90 |
|  | Test 2 |  | 1.0 | 1.0 | / |
| Nickel content |  | [% by weight] | 50.00 | 50.00 | 22.50 |
| Molar amount of nickel |  | [g] | 0.64 | 0.47 | 0.20 |
| Amount of nickel |  | [mmol] | 10.82 | 7.92 | 3.45 |
| Amount of S |  | [mmol] | 1.09 | 1.58 | 0.78 |
| Increase in mass due to uptake of S after 50 h reaction time from TGA analysis Test 1[1] | | [mg] | 35 | 58 | 25 |
| S loading according to chem. analysis Test 1[2] sampling from entire crucible | | [%] [mg] | 1.50 19 | 5.10 47 | 3.20 29 |
| S loading according to chem. analysis Test 2[2] sampling from upper layer of the reactor crucible | | [%] [mg] | 8.1 82 | 12.2 128 | — |
| S loading according to chem. analysis Test 2[2] sampling from middle layer of the reactor crucible | | [%] [mg] | 3.8 39 | 5.2 54 | — |
| S loading according to chem. analysis Test 2[2] sampling from bottom layer of the reactor crucible | | [%] [mg] | 2.7 27.5 | 2.6 27.5 | — |
| S loading according to chem. analysis Test 2[2] average | | [%] [mg] | 4.9 49 | 6.7 70 | — |

[1] Values from TGA
[2] Values from chemical analysis

In the results presented in FIG. 1, the different weights of catalyst in Test 1 were not taken into account. In order to correct this, the results presented in FIG. 3 were normalized to the weight used. The results presented in FIG. 3 show that the catalysts B and C are more suitable for use in sulfur-containing gas streams. In FIG. 3, the x axis corresponds to the uptake of sulfur relative to the mass of nickel present and the y axis corresponds to the catalytic activity. It was postulated here that the sulfur taken up is bound as NiS, but this is not confirmed by analysis but was merely employed for illustration. As FIG. 3 shows, the catalyst B according to the invention displays a higher activity than the catalyst A at the same sulfur loading, while catalyst C displays a similar activity.

The invention claimed is:

1. A process for the methanation of carbon monoxide and/or carbon dioxide, comprising contacting a feed stream containing carbon monoxide and/or carbon dioxide, hydrogen and more than 4 ppb of sulfur with a catalyst comprising aluminum oxide, an Ni active composition and Mn, wherein the molar ratio of Ni/Mn in the catalyst is in the range from 1.0 to 15.0.

2. The process as claimed in claim 1, wherein the catalyst has been produced by coprecipitation.

3. The process as claimed in claim 1, wherein the molar ratio of Ni/Mn in the catalyst is in the range from 2.0 to 6.0.

4. The process as claimed in claim 1, wherein the molar ratio of Al/Ni in the catalyst is in the range from 0.1 to 0.9.

5. The process as claimed in claim 1, wherein the catalyst has been produced by impregnation of aluminum oxide with a solution comprising Ni.

6. The process as claimed in claim 5, wherein the solution comprising Ni also contains Mn.

7. The process as claimed in claim 5, wherein the molar ratio of Ni/Mn in the catalyst is in the range from 6.0 to 10.0.

8. The process as claimed in claim 5, wherein the molar ratio of Al/Ni in the catalyst is in the range from 2 to 9.

9. The process as claimed in claim 1, wherein the feed stream contains more than 10 ppb of sulfur.

10. The process as claimed in claim 1, wherein the feed stream contains from 4 ppb to 100 ppm of sulfur.

11. The process as claimed in claim 1, wherein the Ni active composition has crystallites having a diameter below 20 nm.

12. The process as claimed in claim 1, wherein the catalyst has a $CO_2$ uptake capacity at 35° C. of greater than 200 µmol/g.

13. The process as claimed in claim 1, wherein the catalyst is brought into contact with the feed stream at a temperature above 150° C.

14. The process as claimed in claim 1, wherein the catalyst absorbs at least 90% of the sulfur present in the feed stream.

15. The process as claimed in claim 1, wherein
the molar ratio of Ni/Mn in the catalyst is in the range from 6.0 to 10.0, and
the molar ratio of Al/Ni in the catalyst is in the range from 2 to 9.

16. The process as claimed in claim 1, wherein
the molar ratio of Ni/Mn in the catalyst is in the range from 6.0 to 10.0, and
the molar ratio of Al/Ni in the catalyst is in the range from 2.3 to 5.

17. A process for the methanation of carbon monoxide and/or carbon dioxide, comprising contacting a feed stream containing carbon monoxide and/or carbon dioxide, hydrogen and more than 1 ppb of sulfur with a catalyst comprising aluminum oxide, an Ni active composition and Mn, wherein
the molar ratio of Ni/Mn in the catalyst is in the range from 2.0 to 6.0, and
the molar ratio of Al/Ni in the catalyst is in the range from 0.1 to 0.9.

18. The process as claimed in claim 1, wherein the molar ratio of Ni/Mn in the catalyst is in the range from 3.5 to 5.5.

19. The process as claimed in claim 2, wherein the feed stream contains more than 10 ppb of sulfur.

20. The process as claimed in claim 1, wherein the feed stream contains from 4 ppb to 100 ppm of sulfur.

* * * * *